United States Patent
Akagane (10) Patent No.: US 9,592,072 B2
(45) Date of Patent: Mar. 14, 2017

(54) ULTRASONIC TREATMENT APPARATUS

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/053,768

(22) Filed: Feb. 25, 2016

(65) Prior Publication Data
US 2016/0175000 A1  Jun. 23, 2016

Related U.S. Application Data

(63) Continuation of application No. PCT/JP2014/081594, filed on Nov. 28, 2014.

(30) Foreign Application Priority Data

Feb. 6, 2014  (JP) ................... 2014-021672

(51) Int. Cl.
*A61B 17/32* (2006.01)
*A61B 18/14* (2006.01)
*A61B 18/00* (2006.01)

(52) U.S. Cl.
CPC ...... *A61B 17/320068* (2013.01); *A61B 18/14* (2013.01); *A61B 18/1402* (2013.01);
(Continued)

(58) Field of Classification Search
CPC ............... A61B 17/320068–17/320092; A61B 2017/320072–2017/320096;
(Continued)

(56) References Cited

U.S. PATENT DOCUMENTS 4,043,342 A * 8/1977 Morrison, Jr. ..... A61B 18/1402
606/48
4,674,498 A * 6/1987 Stasz ................. A61B 18/1402
604/22
(Continued)

FOREIGN PATENT DOCUMENTS

JP  S62211057 A  9/1987
JP  H04221539 A  8/1992
(Continued)

OTHER PUBLICATIONS

Jul. 14, 2015 Office Action issued in Japanese Patent Application No. 2015-527381.
(Continued)

*Primary Examiner* — Victor Nguyen
*Assistant Examiner* — Jonathan Hollm
(74) *Attorney, Agent, or Firm* — Oliff PLC (57) ABSTRACT

In an ultrasonic probe, an insulation layer portion is formed on an outer surface of a probe main body portion. A first electrode portion provided on an outer surface of the insulation layer portion so that at least part of the first electrode portion is exposed to an outside in a treatment section, and at least part of a second electrode portion is exposed to the outside in the treatment section. The second electrode portion is electrically insulated from the first electrode portion by the insulation layer portion. The probe main body portion vibrates integrally with the insulation layer portion, the first electrode portion and the second electrode portion.

20 Claims, 7 Drawing Sheets

(52) U.S. Cl.
CPC *A61B 18/149* (2013.01); *A61B 2017/320072* (2013.01); *A61B 2017/320088* (2013.01); *A61B 2018/0097* (2013.01); *A61B 2018/00589* (2013.01); *A61B 2018/00601* (2013.01); *A61B 2018/00994* (2013.01)

(58) Field of Classification Search
CPC ........... A61B 2018/00053–2018/00196; A61B 2018/1246–2018/1293; A61B 2018/1412–2018/1415; A61B 2018/1422; A61B 18/12; A61B 18/14; A61F 9/0074–9/00763; A61C 3/03
USPC .......................................... 606/1, 169, 45–52
See application file for complete search history.

(56) References Cited

U.S. PATENT DOCUMENTS

| | | | | |
|---|---|---|---|---|
| 2003/0073987 | A1* | 4/2003 | Sakurai | A61B 17/320068 606/28 |
| 2006/0241589 | A1* | 10/2006 | Heim | A61B 18/1402 606/48 |
| 2008/0058803 | A1* | 3/2008 | Kimura | A61B 17/320068 606/49 |
| 2009/0318944 | A1* | 12/2009 | Kimura | A61B 17/16 606/169 |
| 2010/0168741 | A1* | 7/2010 | Sanai | A61B 17/320068 606/42 |

FOREIGN PATENT DOCUMENTS

| | | |
|---|---|---|
| JP | H11318919 A | 11/1999 |
| JP | 2001087274 A | 4/2001 |
| JP | 2006187668 A | 7/2006 |
| JP | 2013504396 A | 2/2013 |

OTHER PUBLICATIONS

Feb. 24, 2015 International Search Report issued in International Patent Application No. PCT/JP2014/081594.
Aug. 18, 2016 International Preliminary Report on Patentability issued in PCT/JP2014/081594.

* cited by examiner

F I G. 13 ary electric power; a second electron was also disclosed.

ULTRASONIC TREATMENT APPARATUS

CROSS-REFERENCE TO RELATED APPLICATIONS

This is a Continuation Application of PCT Application No. PCT/JP2014/081594, filed Nov. 28, 2014 and based upon and claiming the benefit of priority from prior Japanese Patent Application No. 2014-021672, filed Feb. 6, 2014, the entire contents of which are incorporated herein by reference.

BACKGROUND OF THE INVENTION

1. Field of Invention

The present invention relates to an ultrasonic probe including a treatment section formed in its distal portion and configured to treat a treatment object with an ultrasonic vibration and a high-frequency electric power, and to an ultrasonic treatment apparatus including the ultrasonic probe.

2. Description of Related Art

Jpn. Pat. Appln. KOKAI Publication No. 2006-187668 discloses an ultrasonic treatment apparatus which treats a treatment object with an ultrasonic vibration and a high-frequency electric power. In this ultrasonic treatment apparatus, an ultrasonic probe configured to transmit an ultrasonic vibration from a proximal side toward a distal side extends along a longitudinal axis, and a treatment section is provided in the distal portion of the ultrasonic probe. The outer peripheral side of the treatment section is covered with a conductive portion. A gap is formed between the treatment section and the conductive portion. Thus, even when the treatment section is vibrated by an ultrasonic vibration, the ultrasonic vibration is not transmitted to the conductive portion, and the conductive portion does not vibrate. By receiving the high-frequency electric power, the treatment section and the conductive portion function as electrodes. Therefore, the ultrasonic treatment apparatus performs an ultrasonic treatment by using the ultrasonic vibration transmitted to the treatment section, and performs a bipolar treatment by using the treatment section and the conductive portion as electrodes.

BRIEF SUMMARY OF THE INVENTION

According to one aspect of the invention, an ultrasonic probe includes that: a probe main body portion which extends along a longitudinal axis, and configured to transmit an ultrasonic vibration from a proximal side toward a distal side; a treatment section provided in a distal portion of the probe main body portion; an insulation layer portion which coats an outer surface of the probe main body portion from the treatment section toward the proximal side; a first electrode portion provided on an outer surface of the insulation layer portion so that at least part of the first electrode portion is exposed to an outside in the treatment section, the first electrode portion having conductivity for conveying a high-frequency electric power, and being configured to apply the high-frequency electric power; a second electrode portion provided so that at least part of the second electrode portion is exposed to the outside in the treatment section, the second electrode portion being configured to function as an electrode different from the first electrode portion, being electrically insulated from the first electrode portion by the insulation layer portion, and being configured to vibrate integrally with the probe main body portion, the insulation layer portion, and the first electrode portion when the probe main body portion transmits the ultrasonic vibration; and a first insulation coating portion formed from the treatment section toward the proximal side, and made of an electrically insulating material, the first insulation coating portion covering the first electrode portion other than an exposed part to the outside in the treatment section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

The first embodiment of the present invention will be described with reference to FIGS. 1 to 6.

Figure 1:
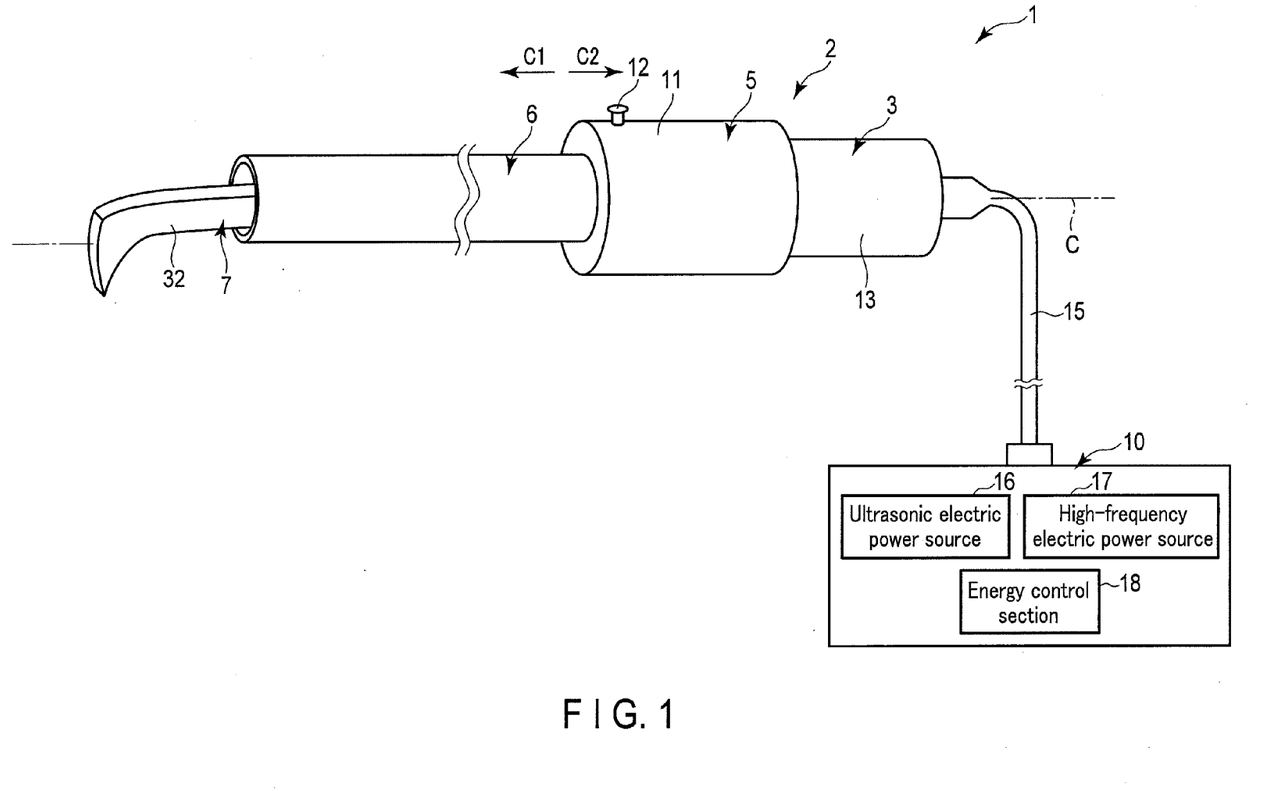
FIG. 1 is a schematic view showing an ultrasonic treatment apparatus according to a first embodiment.

FIG. 1 shows an ultrasonic treatment apparatus 1 of the present embodiment. As shown in FIG. 1, the ultrasonic treatment apparatus 1 includes an ultrasonic treatment instrument 2. The ultrasonic treatment instrument 2 has a longitudinal axis C. One direction parallel to the longitudinal axis C is defined as a distal direction (indicated by arrow C1 in FIG. 1), and a direction opposite to the distal direction is defined as a proximal direction (indicated by arrow C2 in FIG. 1). The distal direction and the proximal direction are collectively called a longitudinal axial direction. In the present embodiment, the ultrasonic treatment device 1 treats a treatment object, such as body tissue, by using a high-frequency electric power (high-frequency current) in addition to an ultrasonic vibration.

The ultrasonic treatment instrument 2 includes a transducer unit 3, a holding unit 5, a sheath 6, and an ultrasonic probe 7. The holding unit 5 includes a cylindrical case portion 11 extending along the longitudinal axis C. An energy operation input button 12, which is an energy operation input section, is attached to the cylindrical case portion 11.

The vibrator unit 3 includes a transducer case 13. By the vibrator case 13 being inserted from the proximal side into the cylindrical case portion 11, the oscillator unit 3 is coupled to the holding unit 5. The proximal portion of the oscillator case 13 is connected to one end of a cable 15. The other end of the cable 15 is connected to a control unit, such as an energy source device. The control unit 10 includes an ultrasonic electric power source 16, a high-frequency electric power source 17, and an energy control section 18. The energy control section 18 is electrically connected to the energy operation input button 12 via an electric path portion (not shown) extending though the transducer case 13 and an inside of the cable 15. The energy control section 18 controls the output condition of an ultrasonic electric power from the ultrasonic electric power source 16, and the output condition of a high-frequency electric power from the high-frequency electric power source 17, based on an input of an energy operation in the energy operation input button 12. The ultrasonic electric power source 16 and the high-frequency electric power source 17 may be separate bodies or one electric power source. The energy control section 18 includes, for example, a central processing unit (CPU) or an application specific integrated circuit (ASIC), and a storage unit, such as a memory.

Figure 2:
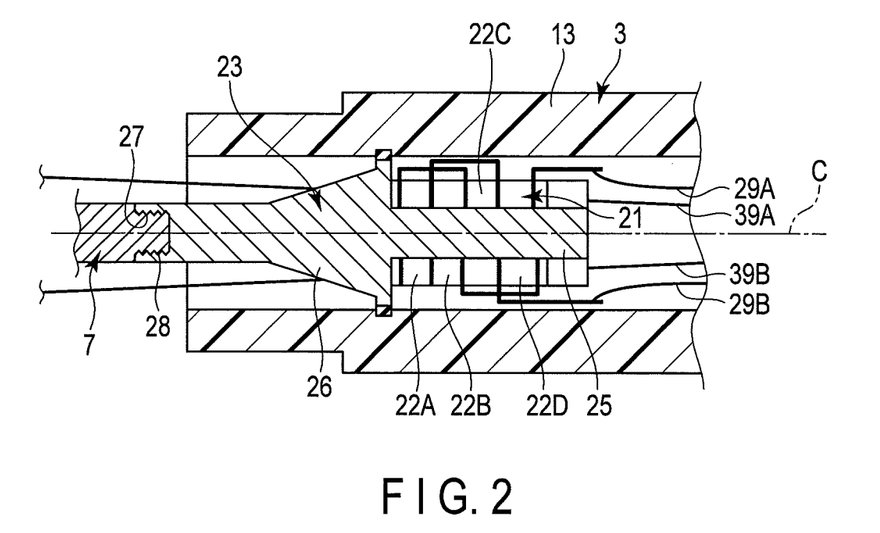
FIG. 2 is a cross-sectional view schematically showing a configuration of a transducer unit according to the first embodiment.

FIG. 2 shows a configuration of the transducer unit 3. As shown in FIG. 2, the transducer unit 3 includes the aforementioned transducer case 13, and an ultrasonic transducer 21, which is a vibration generating section provided in the vibrator case 13. The ultrasonic vibrator 21 includes a plurality of (four in the present embodiment) piezoelectric elements 22A-22D, which convert a current (alternating current) into an ultrasonic vibration. As the ultrasonic electric power is supplied to the ultrasonic transducer 21, the ultrasonic vibration is generated in the ultrasonic oscillator 21.

In the transducer case 13, a horn member 23 extends along the longitudinal axis C. The horn member 23 includes a transducer mounting portion 25. Members forming the ultrasonic oscillator 21, such as piezoelectric elements 22A-22D, are mounted on the oscillator mounting unit 25. The horn member 23 includes a cross-section area changing portion 26. The area of a cross-section in the cross-section area changing portion 26, which is taken perpendicularly to the longitudinal axis C, decreases toward the distal direction. The cross-section area changing portion 26 increases the amplitude of the ultrasonic vibration. An internal thread portion 27 is provided in a distal portion of the horn member 23.

As shown in FIG. 2, an external thread portion 28 is provided in a proximal portion of the ultrasonic probe 7. As the internal thread portion 27 and the external thread portion 28 are screwed together, the ultrasonic probe 7 is connected to the distal side of the horn member 23. The ultrasonic probe 7 extends along the longitudinal axis C. The horn member 23 is connected to the ultrasonic probe 7 inside the cylindrical case portion 11. The ultrasonic transducer 21, which is a vibration generating section, is located on the proximal side with respect to the ultrasonic probe 7.

As shown in FIG. 1, the sheath 6 is coupled to the holding unit 5 by being inserted into the cylindrical case portion 11 from the distal side. Inside the cylindrical case portion 11, the sheath 6 is coupled to the transducer case 13. The ultrasonic probe 7 is inserted through the sheath 6. Thus, the distal portion of the ultrasonic probe 7 protrudes from the distal end of the sheath 6 toward the distal direction.

As shown in FIG. 2, one end of each of electric lines 29A and 29B is connected to the ultrasonic transducer 21. The other end of each of the electric lines 29A and 29B is connected to the ultrasonic electric power source 16 of the control unit 10 through the inside of the cable 15. As the ultrasonic electric power is supplied to the ultrasonic oscillator 21 from the ultrasonic electric power source 16 via the electric lines 29A and 29B, the ultrasonic vibration is generated in the ultrasonic vibrator 21. The generated ultrasonic vibration is transmitted from the ultrasonic transducer 21 via the horn member 23 to the ultrasonic probe 7.

Figure 3:
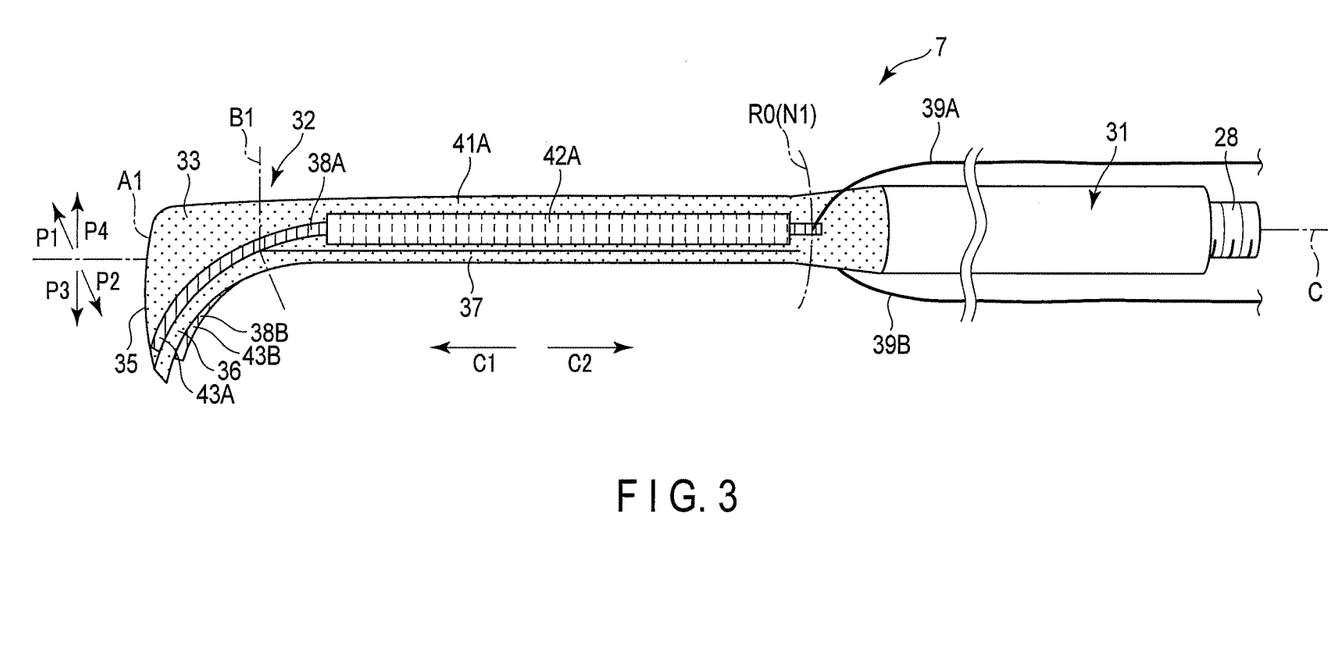
FIG. 3 is a perspective view schematically showing a configuration of an ultrasonic probe according to the first embodiment.
Figure 4:
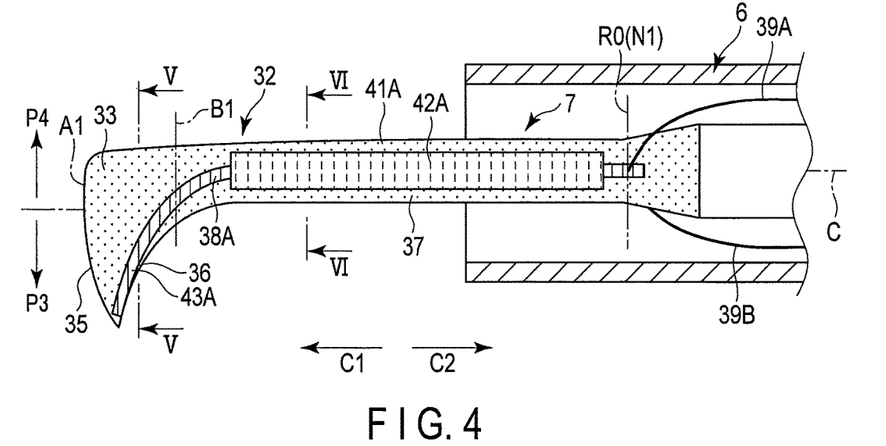
FIG. 4 is a schematic view showing configurations of a distal portion of a sheath and a distal portion of the ultrasonic probe according to the first embodiment.
Figure 5:
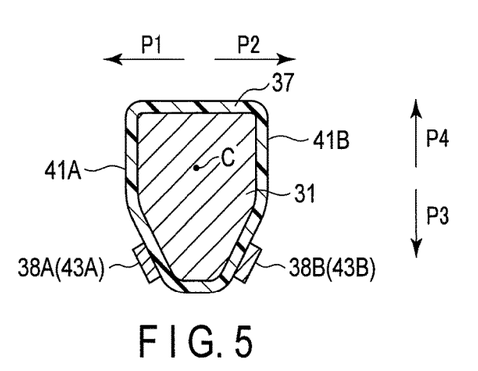
FIG. 5 is a cross-sectional view taken along line V-V in FIG. 4.
Figure 6:
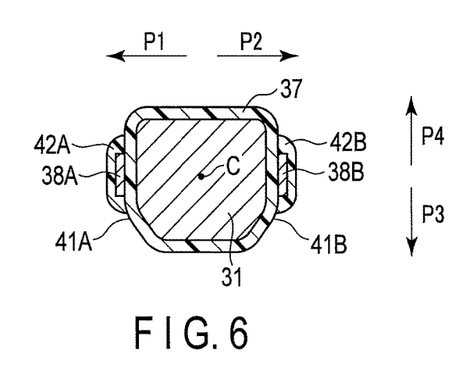
FIG. 6 is a cross-sectional view taken along line VI-VI in FIG. 4.

FIG. 3 shows the ultrasonic probe 7. Herein, one of the directions perpendicular to the longitudinal axis C is defined as a first perpendicular direction (indicated by arrow P1 in FIG. 3), and the direction opposite to the first perpendicular direction is defined as a second perpendicular direction (indicated by arrow P2 in FIG. 3). One of the directions perpendicular to the longitudinal axis C and perpendicular to the first perpendicular direction and the second perpendicular direction is defined as a third perpendicular direction (indicated by arrow P3 in FIG. 3), and the direction opposite to the third perpendicular direction is defined as a fourth perpendicular direction (indicated by arrow P4 in FIG. 3). FIG. 4 shows configurations of the distal portion of the sheath 6 and the distal portion of the ultrasonic probe 7. FIG. 4 shows a cross-section of the sheath 6 taken perpendicularly to the first perpendicular direction and the second perpendicular direction, and shows the ultrasonic probe 7 viewed from the first perpendicular direction. FIG. 5 is a cross-sectional view taken along line V-V in FIG. 4, and FIG. 6 is a cross-sectional view taken along line VI-VI in FIG. 4.

As shown in FIGS. 3-6, the ultrasonic probe 7 includes a probe main body portion 31 extending along the longitudinal axis C. The ultrasonic vibration transmitted to the ultrasonic probe 7 is transmitted through the probe main body portion 31 from the proximal side toward the distal side. By the probe main body portion 31 transmitting the ultrasonic vibration, the ultrasonic probe 7 (probe main body portion 31) vibrates in a longitudinal axial direction parallel to the longitudinal axis (longitudinally oscillates). The ultrasonic probe 7 vibrates at a predetermined resonance frequency (vibrating state) with the distal end of the ultrasonic probe 7 (distal end of the probe main body portion 31) at the most-distal anti-node position A1, which is one of the anti-node positions of the ultrasonic vibration (longitudinal vibration). When the ultrasonic probe 7 vibrates at the predetermined resonance frequency, the most-distal anti-node position A1 is positioned most distally among the anti-node positions of the ultrasonic vibration.

The position where the dimension from the distal end of the probe main body portion 31 toward the proximal side is a ¼ wavelength of the ultrasonic vibration in the state where the ultrasonic probe 7 vibrates at a predetermined resonance frequency is defined as reference position R0. The reference position R0 corresponds to the most-distal node position N1, which is one of the node positions of the ultrasonic vibration (longitudinal oscillation) generated when the ultrasonic probe 7 vibrates at the predetermined resonance frequency. The most-distal node position N1 is located most distally among the node positions of the ultrasonic vibration. The reference position R0 (most-distal node position N1) is located on the proximal side with respect to the distal end of the sheath 6. Therefore, the reference position R0 is located inside the sheath 6.

A treatment section 32 is provided in the distal portion of the probe main body portion 31. The ultrasonic probe 7 is inserted through the sheath 6 with the treatment section 32 protruding from the distal end of the sheath toward the distal direction. The treatment section 32 includes a curved protruding portion 33 which is curved toward the third perpendicular direction with respect to the longitudinal axis C and protrudes toward the third perpendicular direction. In the present embodiment, the curved protruding portion 33 is shaped like a hook. The curved protruding portion 33 includes a protrusion distal surface 35 facing in the distal direction (indicated by arrow C1 in FIG. 3), and a protrusion proximal surface 36 facing in the proximal direction (indicated by arrow C2 in FIG. 3). The protrusion distal surface 35 forms the distal end of the ultrasonic probe 7. A proximal end position of the curved protruding portion 33 is defined as curved proximal end position B1. The curved proximal end position B1 is located on the distal side with respect to the distal end of the sheath 6.

An insulation layer portion 37 is formed on an outer surface of the probe main body portion 31. The insulation layer portion 37 is a coating layer made of an electric insulation material such as resin, and indicated by hatching with dots in FIGS. 3 and 4. The insulation layer portion 37 extends from the treatment section 32 toward the proximal direction. In the present embodiment, the insulation layer portion 37 covers the entire outer surface of the probe main portion 31 in the range expanding in the longitudinal axial direction between the distal end of the ultrasonic probe 7 and the distal end of the sheath 6 (i.e., the treatment section 32). Accordingly, in the present embodiment, the outer surface of the probe main portion 31 is not exposed to the outside even in the treatment section 32 located on the distal side with respect to the distal end of the sheath 6.

The insulation layer portion 37 extends toward the proximal direction beyond the reference position R0 (most-distal node position N1). Thus, the proximal end of the insulation layer portion 37 is on the proximal side with respect to the reference position R0, and on the proximal side with respect to the distal end of the sheath 6. Therefore, the proximal end of the insulation layer portion is located inside the sheath 6. The insulation layer portion 37 is tightly adhered to the outer surface of the probe main body portion 31. By the probe main body portion transmitting the ultrasonic vibration, the insulation layer portion 37 vibrates (longitudinally vibrates) integrally with the probe main body portion 31.

The outer surface of the insulation layer portion 37 is provided with a first conductive coating portion 38A, which is a first electrode portion, and a second conductive coating portion 38B, which is a second electrode portion. The first conductive coating portion 38A and the second conductive coating portion 38B are made of, for example, metallic plating or resin containing silver powder, and are conductive. In FIGS. 3 and 4, the first conductive coating portion 38A and the second conductive coating portion 38B are indicated by hatching with solid lines. One end of a first electric line 39A, which is a first electric path, is connected to the first conductive coating portion 38A. One end of a second electric line 39B, which is a second electric path, is connected to the second conductive coating portion 38B. The first electric line 38A and the second electric line 38B extend through the inside of the sheath 6, the inside of the transducer case 13, and the inside of the cable 15. The other end of the first electric line 39A and the other end of the second electric line 39B are connected to the high-frequency electric power source 17 of the control unit 10. The first electric line 39A and the second electric line 39B are electrically insulated from each other, and are electrically insulated from the probe main body portion 31 and the horn member 23.

The high-frequency electric power is supplied from the high-frequency electric power source 17 via the first electric line 39A to the first conductive coating portion 38A. Accordingly, the first conductive coating portion 38A functions as an electrode (first electrode portion). The high-frequency electric power is supplied from the high-frequency electric power source 17 via the second electric line 39B to the second conductive coating portion 39B. Accordingly, the second conductive coating portion 38B functions as an electrode (second electrode portion) different from the first conductive coating portion 38A. In the state where the first conductive coating portion 38A and the second conductive coating portion 38B function as electrodes, the electric potential of the first conductive coating portion 38A differs from that of the second conductive coating portion 38B.

The insulation layer portion 37 includes a first insulation surface portion 41A having an outer surface facing toward the first perpendicular direction, and a second insulation surface 41B having an outer surface facing in the second perpendicular direction. In the present embodiment, the first conductive coating portion 38A is disposed on the first insulation surface portion 41A, and the second conductive coating portion 38B is disposed on the second insulation surface portion 41B. The insulation layer portion 37 (first insulation surface portion 41A) is provided between the first conductive coating portion 38A and the probe main body portion 31. The insulation layer portion 37 (second insulation surface portion 41B) is provided between the second conductive coating portion 38B and the probe main body unit 31. Accordingly, the first conductive coating portion 38A and the second conductive coating portion 38B are electrically insulated from the probe main body portion 31.

The two directions along the circumference of a circle around the longitudinal axis C are defined as a circumferential direction of the longitudinal axis. The first conductive coating portion 38A and the second conductive coating portion 38B are disposed on the outer surface of the insulation layer portion 37. The first conductive coating portion 38A is separated from the second conductive coating portion 38B in the circumferential direction of the longitudinal direction. Accordingly, the first conductive coating portion 38A and the second conductive coating portion 38B are electrically insulated from each other by the insulation layer portion 37.

The first conductive coating portion 38A is tightly adhered to the insulation layer portion 37 on the first insulation surface portion 41A. By the probe main body portion 31 transmitting the ultrasonic vibration, the first conductive coating portion 38A vibrates (longitudinally oscillates) integrally with the probe main body portion 31 and the insulation layer portion 37. The second conductive coating portion 38B is tightly adhered to the outer surface of the insulation layer portion 37 on the second insulation surface portion 41B. By the probe main body portion 31 transmitting the ultrasonic vibration, the second conductive coating portion 38B vibrates (longitudinally vibrates) integrally with the probe main body portion 31, the insulation layer portion 37, and the first conductive coating portion 38A.

The first conductive coating portion 38A extends from the curved protruding portion 33 toward the proximal direction on the first insulation surface portion 41A. The second conductive coating portion 38B extends from the curved protruding portion 33 in the proximal direction on the second insulation surface portion 41B. The first conductive coating portion 38A and the second conductive coating portion 38B extend toward the proximal direction at least to the reference position R0 (most-distal node position N1). The proximal end of the first conductive coating portion 38A and the proximal end of the second conductive coating portion 38B are located at the reference position R0 or on the proximal side with respect to the reference position R0. Thus, the proximal end of the first conductive coating portion 38A and the proximal end of the second conductive coating portion 38B are located on the proximal side with respect to the distal end of the sheath 6, and are located inside the sheath 6. The proximal end of the first conductive coating portion 38A and the proximal end of the second conductive coating portion. 38B are located on the distal side with respect to the proximal end of the insulation layer portion 37. Therefore, no part of the first conductive coating portion 38A comes into contact with the probe main body portion 31. Similarly, no part of the second conductive coating portion 38B comes into contact with the probe main body portion 31.

One end of the first electric line 39A is connected to the first conductive coating portion 38A at the reference position R0 (or in vicinity of the reference position R0). One end of the second electric line 39B is connected to the second conductive coating portion 38B at the reference position R0 (or in vicinity of the reference position R0). The reference position R0 corresponds to the most-distal node position N1 in the state where the ultrasonic probe 7 vibrates at the predetermined resonance frequency. Therefore, the amplitude of ultrasonic vibration (longitudinal vibration) is zero at the reference position R0. In vicinity of the reference position R0, the amplitude of ultrasonic vibration is small. Therefore, even when the first conductive coating portion 38A and the second conductive coating portion 38B oscillate integrally with the probe main body portion 31, the first electric line 39A is firmly connected to the first conductive coating portion 38A, and the second electric line 39B is firmly connected to the second conductive coating portion 38B.

The ultrasonic probe 7 includes a first insulation coating portion 42A which covers the outer surface of the first conductive coating portion 38A, and a second insulation coating portion 42B which covers the outer surface of the second conductive coating portion 38B. The first insulation coating portion 42A and the second insulation coating portion 42B are made of an electric insulation material, such as resin, and are indicated by hatching with broken lines in FIGS. 3 and 4. The distal end of the first insulation coating portion 42A is located on the proximal side with respect to the curved proximal end position B1. Thus, in the curved protruding portion 33, the first conductive coating portion 38A is exposed to the outside to form a first conductor-exposed portion 43A. The distal end of the second insulation coating portion 42A is located on the proximal side with respect to the curved proximal end position B1. Thus, in the curved protruding portion 33, the second conductive coating portion 38B is exposed to the outside to form a second conductor-exposed portion 43A. When the treatment object such as body tissue is in contact with the protrusion proximal surface 36 of the curved protruding portion 33, the treatment target comes into contact with the first conductor-exposed portion 43A and the second conductor-exposed portion 43B.

The distal end of the first insulation coating portion 42A and the distal end of the second insulation coating portion 42B are located on the distal side with respect to the distal end of the sheath 6. The proximal end of the first insulation coating portion 42A and the proximal end of the second insulation coating portion 42B are located on the proximal side with respect to the distal end of the sheath 6. Thus, the first conductive coating portion 38A is not exposed to the outside except for the first conductor-exposed portion 43A. Namely, in the treatment section 32 positioned on the distal side with respect to the distal end of the sheath 6, a part (first conductor-exposed portion 43A) of the first conductive coating portion 38A is exposed to the outside. Similarly, the second conductive coating portion 38B is not exposed to the outside except for the second conductor-exposed portion 43B. Namely, in the treatment section 32 positioned on the distal side with respect to the distal end of the sheath 6, a part (second conductor-exposed portion 43B) of the second conductive coating portion 38B is exposed to the outside. Accordingly, body tissue or the like different from the treatment object does not come into contact with the first conductive coating portion (first electrode portion) 38A except for the first conductor-exposed portion 43A, and does not come into contact with the second conductive coating portion (second electrode portion) 38B except for the second conductor-exposed portion 43B.

The proximal end of the first insulation coating portion 42A and the proximal end of the second insulation coating portion 42B are located on the distal side with respect to the reference position R0 (most-distal node position N). Thus, the outer surface of the first conductive coating portion 38A is not covered with the first insulation coating portion 42A at the reference position R0, where the first electric line 39A is connected to the first conductive coating portion 38A. Therefore, the high-frequency electric power is reliably supplied from the first electric line 39A to the first conductive coating portion 38A. Similarly, the outer surface of the second conductive coating portion 39B is not covered with the second insulation coating portion 42B at the reference position R0, where the second electric line 39B is connected to the second conductive coating portion 38B. Therefore, the high-frequency electric power is reliably supplied from the second electric line 39B to the second conductive coating portion 38B.

Next, the function and advantageous effect of the ultrasonic probe 7 and the ultrasonic treatment apparatus 1 according to the present embodiment will be described. When the treatment object such as body tissue (blood vessel) is treated by using the ultrasonic treatment apparatus 1, the ultrasonic probe 7 and the sheath 6 are inserted into a body cavity. Then, the protrusion proximal surface 36 of the curved protruding portion 33 of the treatment section 32 is brought into contact with the treatment target. The first conductor-exposed portion 43A of the first conductive coating portion (first electrode portion) 38A and the second conductor-exposed portion 43B of the second conductive coating portion (second electrode portion) 38B are thereby brought into contact with the treatment object. In this state, an energy operation is input at the energy operation input button 12. The energy control section 18 thereby controls the ultrasonic electric power source 16 to output an ultrasonic electric power and the high-frequency electric power source 17 to output a high-frequency electric power.

As the ultrasonic electric power is supplied to the ultrasonic transducer 21, an ultrasonic vibration is generated in the ultrasonic vibrator 21. The generated ultrasonic vibration is transmitted to the ultrasonic probe 7 via the horn member 23. In the ultrasonic probe 7 (probe main body portion 31), the ultrasonic vibration is transmitted from the proximal direction toward the distal direction to the treatment section 32, and the probe main body unit 31 vibrates (longitudinally vibrates) at a predetermined resonance frequency. At this time, the insulation layer portion 37, the first conductive coating portion (first electrode portion) 38A and the second conductive coating portion (second electrode portion) 38B vibrate integrally with the probe main body portion 31. By receiving the high-frequency electric power from the high-frequency electric power source 17, the first conductive coating portion 38A functions as an electrode (first electrode portion). By receiving the high-frequency electric power from the high-frequency electric power source 17, the second conductive coating portion 38B functions as an electrode (second electrode portion) different from the first conductive coating portion 38A. At this time, the electric potential of the first conductive coating portion 38A differs from that of the second conductive coating portion 38B.

By the treatment section 32 vibrating (longitudinally vibrating) with the protrusion proximal surface 36 of the curved protruding portion 33 in contact with the treatment object, the treatment object is incised. Since the first conductor-exposed portion 43A and the second conductor-exposed portion 43B are in contact with the treatment target, a high-frequency current flows between the first conductive coating portion 38A and the second conductive coating portion 38B via the treatment object, and a bipolar treatment using the first conductive coating portion 38A and the second conductive coating portion 38B as electrodes is performed. As the high-frequency current flows through the treatment object, the treatment object is denatured and coagulated. In the above-described manner, the treatment object is incised (cut) and coagulated (sealed) at the same time.

The first conductive coating portion 38A and the second conductive coating portion 38B vibrate integrally with the probe main body unit 31. Therefore, even in the bipolar treatment in which the first conductive coating portion (first electrode portion) 38A and the second conductive coating portion (second electrode portion) 38B come into contact with the treatment object, the treatment object is prevented from adhering to the first conductor-exposed portion 43A and to the second conductor-exposed portion 43B. Accordingly, in the treatment using the ultrasonic vibration and the high-frequency electric power, treatment performance can be properly ensured.

In addition, the proximal end of the first conductive coating portion 38A, and the proximal end of the second conductive coating portion 38B are located on the distal side with respect to the proximal end of the insulation layer portion 37. Thus, no part of the first conductive coating portion 38A comes into contact with the probe main body portion 31, and no part of the second conductive coating portion 38B comes into contact with the probe main body portion 31. Consequently, in the bipolar treatment using the high-frequency electric power, a high-frequency current is effectively prevented from flowing through the portions (such as the probe main body portion 31) other than the treatment object between the first conductive coating portion (first electrode portion) 38A and the second conductive coating portion (second electrode portion) 38B. Accordingly, in the bipolar treatment, the current density of the high-frequency current flowing through the treatment object increases, and treatment performance increases.

One end of the first electric line 39A is connected to the first conductive coating portion 38A at the reference position R0 (most-distal node position N1), and one end of the second electric line 39B is connected to the second conductive coating portion 38B at the reference position R0 (most-distal node position N1). Therefore, even when the first conductive coating portion 38A and the second conductive coating portion 38B vibrate integrally with the probe main body portion 31, the first electric line 39A is firmly connected to the first conductive coating portion 38A, and the second electric line 39B is firmly connected to the second conductive coating portion 38B. Consequently, the high-frequency electric power can be properly supplied from the first electric line 39A to the first conductive coating portion 38A, and can be properly supplied from the second electric line 39B to the second conductive coating portion 38B.

The first insulation coating portion 42A prevents the first conductive coating portion 38A from being exposed to the outside except for the first conductor-exposed portion 43A. Similarly, the second insulation coating portion 42B prevents the second conductive coating portion 38B from being exposed to the outside except for the second conductor-exposed portion 43B. Accordingly, in the bipolar treatment using a high-frequency current, body tissue or the like different from the treatment object does not come into contact with the first conductive coating portion (first electrode portion) 38A except for the first conductor-exposed portion 43A, and does not come into contact with the second conductive coating portion (second electrode portion) 38B except for the second conductor-exposed portion 43B. Consequently, treatment performance can be increased in the bipolar treatment.

In addition, the outer surface of the first conductive coating portion 38A is not covered with the first insulation coating portion 42A at the reference position R0, where the first electric line 39A is connected to the first conductive coating portion 38A. Similarly, the outer surface of the second conductive coating portion 39B is not covered with the second insulation coating portion 42B at the reference position R0, where the second electric line 39B is connected to the second conductive coating portion 38B. Therefore, the high-frequency electric power can be reliably supplied from the first electric line 39A to the first conductive coating portion 38A, and can be reliably supplied from the second electric line 39B to the second conductive coating portion 38B.

Modifications

Figure 7:
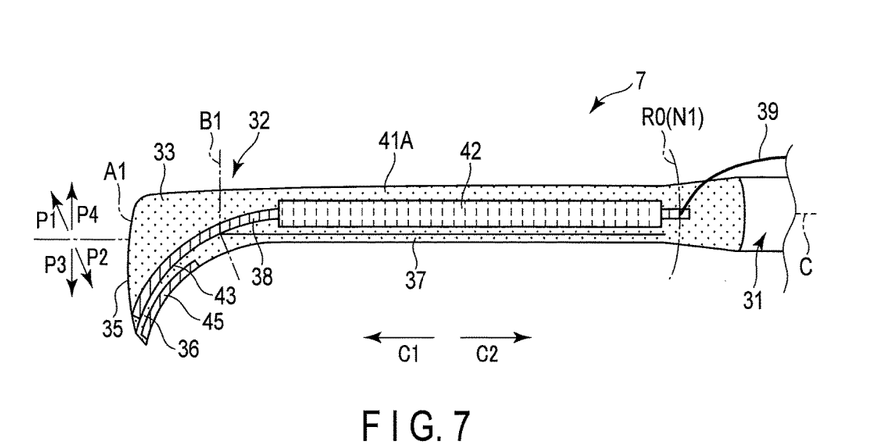
FIG. 7 is a perspective view schematically showing a configuration of a distal portion of an ultrasonic probe according to a first modification.
Figure 8:
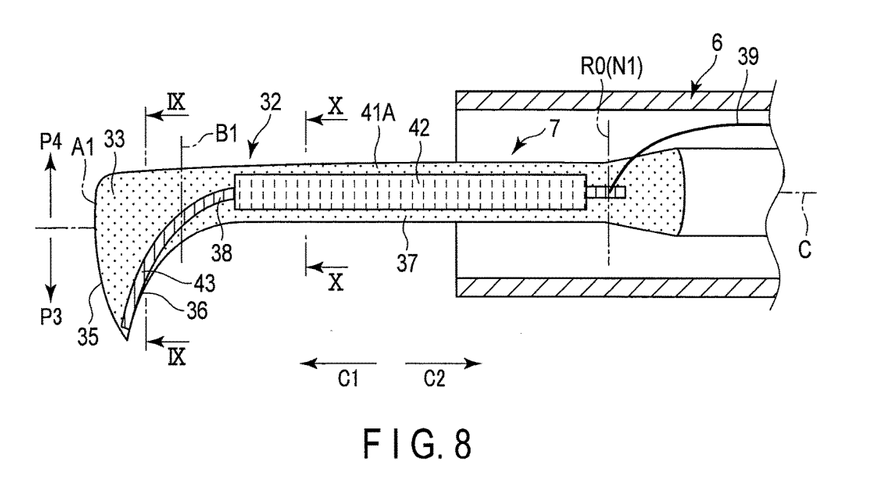
FIG. 8 is a schematic view showing configurations of a distal portion of a sheath and a distal portion of the ultrasonic probe according to the first modification.
Figure 9:
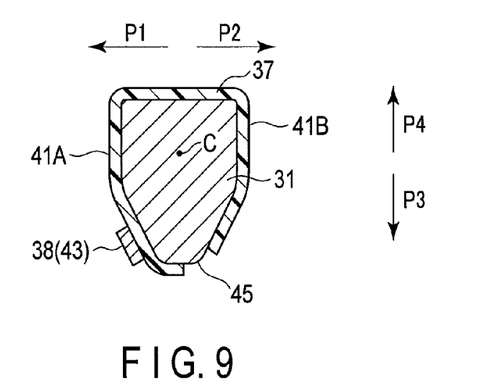
FIG. 9 is a cross-sectional view taken along line IX-IX in FIG. 8.
Figure 10:
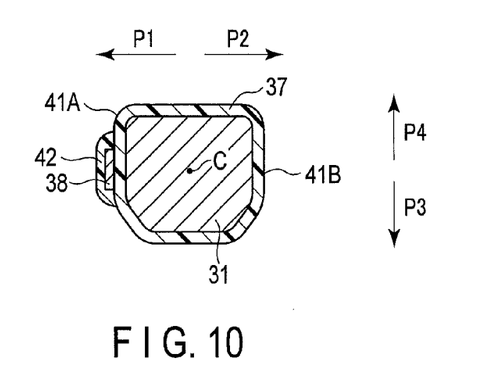
FIG. 10 is a cross-sectional view taken along line X-X in FIG. 8.

In the first embodiment, two conductive coating portions (38A and 38B) which function as electrodes are provided. However, it is not limited. For example, as a first modification, one conductive coating portion 38 may be provided as shown in FIGS. 7 to 10. FIG. 7 shows a distal portion of the ultrasonic probe 7, and FIG. 8 shows a distal portion of the ultrasonic probe 7 and a distal portion of the sheath 6. FIG. 9 is a cross-sectional view taken along line IX-IX in FIG. 8, and FIG. 10 is a cross-sectional view taken along line X-X in FIG. 8. FIG. 8 shows a cross-section of the sheath 6 taken perpendicularly to the first perpendicular direction and the second perpendicular direction, and shows the ultrasonic probe 7 viewed from the first perpendicular direction. In FIGS. 7 and 8, the insulation layer portion 37 is indicated by hatching with dots, and the conductive coating portion 38 is indicated by hatching with solid lines.

The conductive coating portion 38 has a configuration almost the same as that of the first conductive coating portion 38A in the first embodiment, and is a first electrode portion which functions as an electrode by receiving a high-frequency electric power. Namely, the conductive coating portion 38 vibrates (longitudinally oscillates) integrally with the probe main body portion 31. The conductive coating portion 38 is disposed on the outer surface of the insulation layer portion 37. The insulation layer portion 37 extends toward the proximal direction beyond the reference position R0 (most-distal node position N1), and the conductive coating portion 38 extends toward the proximal direction at least to the reference position R0. The proximal end of the conductive coating portion 38 is located inside the sheath 6, and located on the distal side with respect to the proximal end of the insulation layer portion 37.

One end of an electric line 39, which is an electric path, is connected to the conductive coating portion 38 at the reference position R0 (or in vicinity of the reference position R0). The electric line 39 has a configuration almost the same as that of the first electric line 39A in the first embodiment. Namely, the other end of the electric line 39 is connected to the high-frequency electric power source 17 of the control unit 10. The high-frequency electric power is supplied from the high-frequency electric power source 17 via the electric line 39 to the conductive coating portion 38.

The outer surface of the conductive coating portion 38 is covered with an insulation coating portion 42. The insulation coating portion 42 has a configuration almost the same as that of the first insulation coating portion 42A in the first embodiment. Thus, the distal end of the insulation coating portion 42 is located on the proximal side with respect to the curved proximal end position B1 and, in the curved protruding portion 33, the conductive coating portion 38 is exposed to the outside to form a conductor-exposed portion 43. When treatment is performed with the protrusion proximal surface 36 of the curved protruding portion 33 brought into contact with the treatment object, the conductor-exposed portion 43 is brought into contact with the treatment object. The distal end of the insulation coating portion 42 is located on the distal side with respect to the distal end of the sheath 6, and the proximal end of the insulation coating portion 42 is located inside the sheath 6. The proximal end of the insulation coating portion 42 is located on the distal side with respect to the reference position 0 (most-distal node position N). In FIGS. 7 and 8, the insulation coating portion 42 is indicated by hatching with broken lines.

Unlike in the first embodiment, the insulation layer portion 37 covers only part of the outer surface, not the entire outer surface, of the probe main bod portion 31 in the range expanding in the longitudinal axial direction between the distal end of the ultrasonic probe 7 and the distal end of the sheath 6 (i.e., the treatment section 32) in the present modification. Additionally, in the present modification, the outer surface of the probe main body portion 31 is exposed to the outside on a part of the protrusion proximal surface 36 of the curved protruding portion 33. A main body exposed portion 45, which is exposed to the outside on the protrusion proximal surface 36 of the treatment section 32, is provided on the outer surface of the probe main body portion 31. The main body exposed portion 45 is not covered with the insulation layer portion 37. In FIG. 7, the main body exposed portion 45 is indicated by hatching with solid lines.

In the present modification, one end of an electric line (not shown) is connected to the proximal portion of the horn member 23. The electric line extends thorough the inside of the cable 15, and the other end of the electric line is connected to the high-frequency electric power source 17. The high-frequency electric power is supplied from the high-frequency electric power source 17 via the electric line (not shown), the horn member 23, and the probe main body portion 31 to the main body exposed portion 45. By receiving the high-frequency electric power, the main body exposed portion 45 functions as an electrode (second electrode portion) different from the conductive coating portion (first electrode portion) 38. When treatment is performed with the protrusion proximal surface 36 of the curved protruding portion 33 brought into contact with the treatment object, the main body exposed portion 45 is brought into contact with the treatment target.

In the curved protruding portion 33, the main body exposed portion 45 is separated from the conductive coating portion 38. Between the conductive coating portion 38 and the probe main body portion 31, the insulation layer portion 37 is provided, and the conductive coating portion is electrically insulated from the probe main body portion 31. Accordingly, the conductive coating portion (first electrode portion) 38 and the main body exposed portion (second electrode portion), 45 are electrically insulated from each other by the insulation layer portion 37. Since the main body exposed portion 45 is part of the probe main body portion 31, the main body exposed portion 45 vibrates (longitudinally vibrates) integrally with the probe main body portion 31.

As in the first embodiment, by the treatment section vibrating (longitudinally oscillating) with the protrusion proximal surface 36 of the curved protruding portion 33 in contact with the treatment object, the treatment object is incised in the present modification. As the protrusion proximal surface 36 of the curved protruding portion 33 is brought into contact with the treatment object, the conductor-exposed portion 43 of the conductive coating portion 38 and the main body exposed portion 45 are brought into contact with the treatment object. Thus, a high-frequency current flows between the conductive coating portion 38 and the main body exposed portion 45 via the treatment target, and bipolar treatment using the conductive coating portion 38 and the main body exposed portion 45 as electrodes is performed. As the high-frequency current flows through the treatment object, the treatment object is coagulated. In the above-described manner, the treatment object is incised (cut) and coagulated (sealed) at the same time.

The conductive coating portion 38 and the main body exposed portion 45 vibrate integrally with the probe main body unit 31. Therefore, even in the bipolar treatment in which the conductive coating portion (first electrode portion) 38 and the main body exposed portion (second electrode portion) 45 come into contact with the treatment object, the treatment object is effectively prevented from adhering to the conductor-exposed portion 43 and to the main body exposed portion 45. Accordingly, in the treatment using the ultrasonic vibration and the high-frequency electric power, treatment performance can be properly ensured. The present modification also performs the same advantage as the first embodiment.

Figure 11:
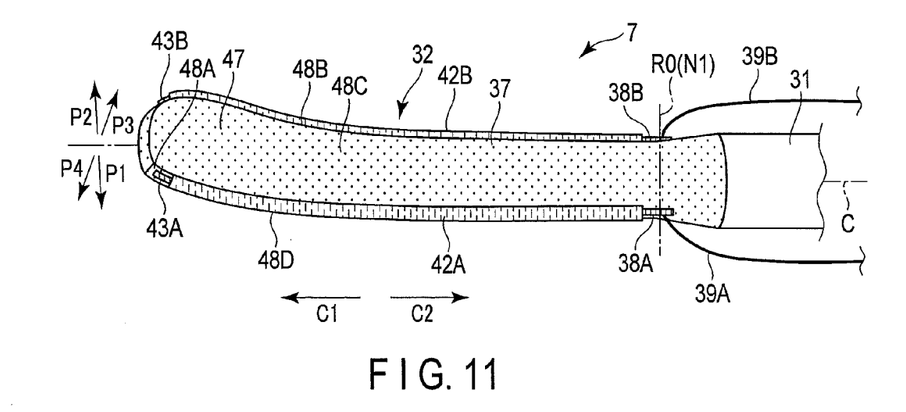
FIG. 11 is a perspective view schematically showing a configuration of a distal portion of an ultrasonic probe according to a second modification.
Figure 12:
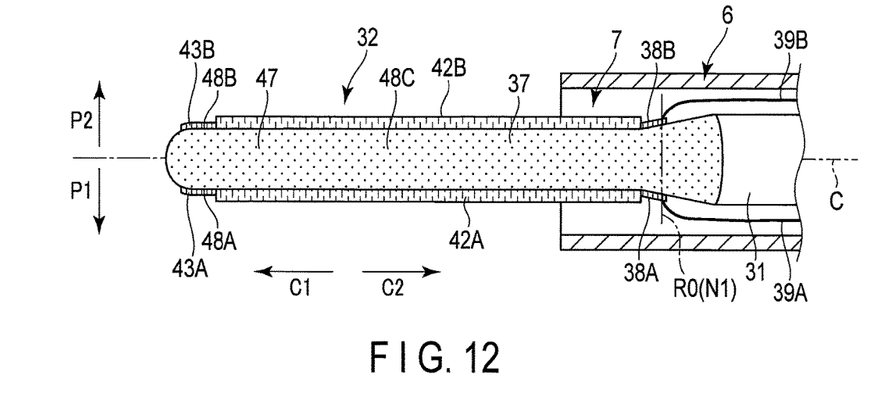
FIG. 12 is a schematic view showing configurations of a distal portion of a sheath and a distal portion of the ultrasonic probe according to the second modification.

As a second modification, the curved protruding portion 33 shaped like a hook need not be provided in the treatment section 32, as shown in FIGS. 11 and 12. In the present modification, the treatment section 32 is shaped like a spatula. In the present modification, the first perpendicular direction (indicated by arrow P1 in FIG. 11), the second perpendicular direction (indicated by arrow P2 in FIG. 11), the third perpendicular direction (indicated by arrow P3 in FIG. 11), and the fourth perpendicular direction (indicated by arrow P4 in FIG. 11) are defined in the same manner as in the first embodiment. The treatment section 32 includes a curved extending portion 47 which is curved in the third and fourth perpendicular directions with respect to the longitudinal axis C. The curved extending portion 47 forms the distal end of the ultrasonic probe 7. In the treatment section 32 shaped like a spatula, the dimension in the first and second perpendicular directions is greater than that in the third and fourth directions.

As in the first embodiment, the insulation layer portion 37 covers the entire outer surface of the probe main portion 31 in the range expanding in the longitudinal axial direction between the distal end of the ultrasonic probe 7 and the distal end of the sheath 6 (i.e., the treatment section 32) in the present modification. The insulation layer portion 37 extends in the proximal direction beyond the reference position R0 (most-distal node position N1). The insulation layer portion 37 includes a first insulation surface portion 48A having an outer surface facing toward the first perpendicular direction, a second insulation surface portion 48B having an outer surface facing in the second perpendicular direction, a third insulation surface portion 48C having an outer surface facing toward the third perpendicular direction, and a fourth insulation surface portion 48D having an outer surface facing toward the fourth perpendicular direction.

In the present modification, the first conductive coating portion 38A, which is the first electrode portion, is disposed on the first insulation surface portion 48A, and the second conductive coating portion 38B, which is the second electrode portion, is disposed on the second insulation surface portion 48B. The first insulation coating portion 42A covers the outer surface of the first conductive coating portion 38A so that the first conductor-exposed portion 43A of the first conductive coating portion 38A is exposed to the outside on the curved extending portion 47. The second insulation coating portion 42B covers the outer surface of the second conductive coating portion 38B so that the second conductor-exposed portion 43B of the second conductive coating portion 38B is exposed to the outside on the curved extending portion 47.

Figure 13:
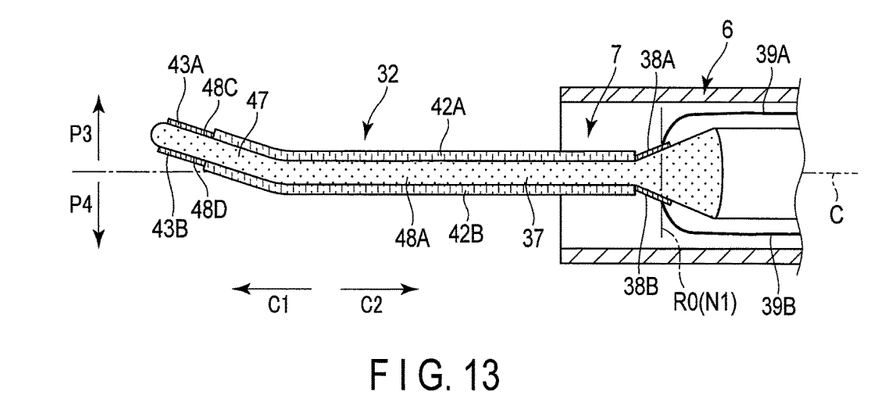
FIG. 13 is a schematic view showing configurations of a distal portion of a sheath and a distal portion of an ultrasonic probe according to a third modification.

As a third modification (modification of the second modification), in the treatment section 32 shaped like a spatula, the first conductive coating portion 38A, which is the first electrode portion, may extend to the third insulation surface portion 48C, and the second conductive coating portion 38B, which is the second electrode portion, may extend to the fourth insulation surface portion 48D, as shown in FIG. 13.

As in the first embodiment, the first conductive coating portion 38A and the second conductive coating portion 38B are electrically insulated from each other by the insulation layer portion 37 in the second modification and the third modification. Therefore, the second modification and the third modification perform the same advantage as the first embodiment. In FIGS. 11 to 13, the insulation layer portion 37 is indicated by hatching with dots, the first conductive coating portion 38A and the second conductive coating portion 38B are indicated by hatching with solid lines, and the first insulation coating portion 42A and the second insulation coating portion 42B are indicated by hatching with broken lines.

In the above-described embodiment and modifications, an insulation layer portion (such as element 37) is formed on the outer surface of the probe main body portion (such as element 31) toward the proximal direction (such as direction C2) from the treatment section (such as element 32). The first electrode portion (such as element 38A or 38) is provided on the outer surface of the insulation layer portion (such as element 37) so that, in the treatment section (such as element 32), at least part of the first electrode portion is exposed to the outside. The second electrode portion (such as element 38B or 45) is provided so that, in the treatment section (such as element 32), at least part of the second electrode portion is exposed to the outside. The first electrode portion (such as element 38A or 38) and the second electrode portion (such as element 38B or 45) function as electrodes which receive the high-frequency electric power, and are electrically insulated from each other by the insulation layer portion (such as element 37). By the Probe main body portion (such as element 31) transmitting the ultrasonic vibration, the probe main body portion (such as element 31) vibrates integrally with the insulation layer portion (such as element 37), the first electrode portion (such as element 38A or 38) and the second electrode portion (such as element 38B or 45).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An ultrasonic treatment apparatus comprising:
a probe main body portion of an ultrasonic probe extending along a longitudinal axis, the probe main body portion being configured to transmit an ultrasonic vibration from a proximal side toward a distal side;
a treatment section provided in a distal portion of the probe main body portion;
an insulation layer extending on an outer surface of the probe main body portion from the treatment section toward the proximal side;
a first electrode provided on an outer surface of the insulation layer, at least an end portion of the first electrode in the treatment section being exposed to an outside, the first electrode having conductivity for conveying a high-frequency electric power;
a second electrode having at least an end portion of the second electrode in the treatment section exposed to the outside, the second electrode being configured to function as an electrode different from the first electrode, the second electrode being electrically insulated from the first electrode by the insulation layer, and the second electrode being configured to vibrate integrally with the probe main body portion, the insulation layer, and the first electrode when the probe main body portion transmits the ultrasonic vibration;
a first insulation coating extending from the treatment section toward the proximal side, the first insulation coating terminating prior to the end portion of the first electrode, the first insulation coating being made of an electrically insulating material, the first insulation coat- ing covering the first electrode other than an exposed part to the outside in the treatment section;
a first electric line having one end connected to the first electrode, the high-frequency electric power being supplied to the first electrode portion via the first electric line; and
an ultrasonic transducer configured to generate the ultrasonic vibration and to transmit the generated ultrasonic vibration to the probe main body portion so that the probe main body portion vibrates at a predetermined resonance frequency.

2. The ultrasonic treatment apparatus of claim 1, wherein the second electrode is formed on the outer surface of the probe main portion so that the second electrode is exposed to the outside in the treatment section, and the second electrode is supplied with the high-frequency electric power via the probe main body portion.

3. The ultrasonic treatment apparatus of claim 1 further comprising:
an ultrasonic electric power source configured to generate an ultrasonic electric power supplied to the ultrasonic transducer; and
a high-frequency electric power source configured to generate the high frequency electric power supplied to the first electrode and the second electrode.

4. The ultrasonic treatment apparatus of claim 1, wherein the first electrode is configured to apply the high-frequency electric power through the exposed part to the outside in the treatment section.

5. The ultrasonic treatment apparatus of claim 1, wherein the probe main body portion vibrates at the predetermined resonance frequency so that one of vibration nodes is located at a connecting position of the first electric line to the first electrode portion.

6. The ultrasonic treatment apparatus of claim 5, wherein:
the insulation layer extends to a position located on the proximal side with respect to the connecting position of the first electric line; and
a proximal end of the first electrode is located on the distal side with respect to a proximal end of the insulation layer.

7. The ultrasonic treatment apparatus of claim 6, wherein:
the first electrode extends toward the proximal side at least to the connecting position of the first electric line; and
a proximal end of the first insulation coating is located on the distal side with respect to the connection position of the first electric line.

8. The ultrasonic treatment apparatus of claim 7 further comprising:
a high-frequency electric power source connected to another end of the first electric line, the high-frequency electric power source being configured to generate the high-frequency electric power supplied to the first electrode and the second electrode, the high-frequency electric power source being configured to supply the high-frequency electric power to the first electrode via the first electric line.

9. The ultrasonic treatment apparatus of claim 7 further comprising:
a sheath through which the ultrasonic probe is inserted so that the treatment section protrudes toward the distal side, and inside which the proximal end of the first insulation coating is located.

10. The ultrasonic treatment apparatus of claim 6 further comprising:
a sheath through which the ultrasonic probe is inserted so that the treatment section protrudes toward the distal side, and inside which the proximal end of the insulation layer is located.

11. The ultrasonic treatment apparatus of claim 5, wherein the probe main body portion vibrates at the predetermined resonance frequency so that a most-distal vibration node located most distally among the vibration nodes is located at the connecting position of the first electric line to the first electrode portion.

12. The ultrasonic treatment apparatus of claim 11, wherein the second electrode is provided on the outer surface of the insulation layer.

13. The ultrasonic treatment apparatus of claim 12, further comprising:
a second electric line having one end connected to the second electrode, the high-frequency electric power being configured to be supplied to the second electrode via the second electric line, wherein
the most-distal vibration node is located at a connecting position of the second electric line to the second electrode when the probe main body portion vibrates at the predetermined resonance frequency.

14. The ultrasonic treatment apparatus of claim 13, wherein:
the insulation layer extends to a position located on the proximal side with respect to the connection position of the first electric line and the connection position of the second electric line; and
a proximal end of the first electrode and a proximal end of the second electrode are located on the distal side with respect to a proximal end of the insulation layer.

15. The ultrasonic treatment apparatus of claim 14 further comprising a second insulation coating extending from the treatment section toward the proximal side, the second insulation coating terminating prior to a distal end portion of the second electrode, the second insulation coating being made of an electrically insulating material, the second insulation coating covering the second electrode other than an exposed part to the outside in the treatment section.

16. The ultrasonic treatment apparatus of claim 15, wherein:
the first electrode extends toward the proximal side at least to the connecting position of the first electric line; and
a proximal end of the second insulation coating is located on the distal side with respect to the connecting position of the second electric line.

17. The ultrasonic treatment apparatus of claim 16 further comprising:
a high-frequency electric power source connected to the other end of the first electric line and another end of the second electric line, the high-frequency electric power source being configured to generate the high-frequency electric power supplied to the first electrode and the second electrode, and the high-frequency electric power source being configured to supply the high-frequency electric power to the first electrode via the first electric line and to the second electrode via the second electric line.

18. The ultrasonic treatment apparatus of claim 16 further comprising:
a sheath through which the ultrasonic probe is inserted so that the treatment section protrudes toward the distal side, and inside which the proximal end of the first insulation coating and the proximal end of the second insulation coating are located.

19. The ultrasonic treatment apparatus of claim 12, wherein:
- when one of directions perpendicular to the longitudinal axis is a first perpendicular direction, and a direction opposite to the first perpendicular direction is a second perpendicular direction, the insulation layer includes a first insulation surface in which the outer surface of the insulation layer faces toward the first perpendicular direction, and a second insulation surface in which the outer surface of the insulation layer faces toward the second perpendicular direction;
- the first electrode is provided on the first insulation surface; and
- the second electrode is provided on the second insulation surface.

20. The ultrasonic treatment apparatus of claim 19, wherein:
- when one of directions perpendicular to the longitudinal axis and perpendicular to the first perpendicular direction and the second perpendicular direction is a third perpendicular direction, the treatment section includes a curved protruding portion curved toward the third perpendicular direction with respect to the longitudinal axis, and protruding toward the third perpendicular direction;
- the first electrode extends from the curved protruding portion toward the proximal side on the first insulation surface; and
- the second electrode extends from the curved protruding portion toward the proximal side on the second insulation surface.

* * * * *